United States Patent [19]

Rüger et al.

[11] Patent Number: 4,845,099
[45] Date of Patent: Jul. 4, 1989

[54] TETRAHYDROQUINOLINE DERIVATIVES, THEIR USE AND PHARMACEUTICAL FORMULATIONS CONTAINING THEM

[75] Inventors: Wolfgang Rüger, Kelkheim; Gerd Driesen, Wiesbaden; Helmut Bohn, Schöneck; Piero Martorana, Bad Homburg, all of Fed. Rep. of Germany

[73] Assignee: Cassella Aktiengesellschaft, Frankfurt, Fed. Rep. of Germany

[21] Appl. No.: 99,760

[22] Filed: Sep. 22, 1987

[30] Foreign Application Priority Data

Oct. 6, 1986 [DE] Fed. Rep. of Germany ....... 3633977

[51] Int. Cl.$^4$ ............. A61K 31/495; C07D 401/14
[52] U.S. Cl. ............................... 514/253; 514/235.2; 514/245; 514/311; 514/314; 544/121; 544/212; 544/295; 544/363; 546/165
[58] Field of Search ............ 544/363, 295, 212, 121; 546/165; 514/253, 245, 311, 314, 235.2

[56] References Cited

U.S. PATENT DOCUMENTS 4,335,123 6/1982 Grawinger et al. ............ 546/165

OTHER PUBLICATIONS

Hori, et al., "Chemical Abstracts", vol. 68, 1968, col. 2796s.

*Primary Examiner*—Richard L. Raymond
*Assistant Examiner*—James H. Turnipseed
*Attorney, Agent, or Firm*—Perman & Green

[57] ABSTRACT

Derivatives of tetrahydroquinoline of the formula I

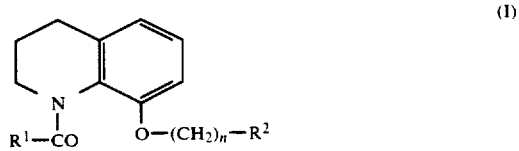

(I)

and acid addition salts thereof, wherein n denotes 2, 3, 4, 5 or 6, $R^1$ denotes, for example, alkyl, phenyl or pyridyl, $R^2$ denotes the radical

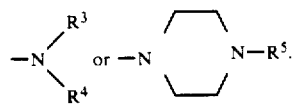

$R^3$ and $R^4$ independently of one another denote, for example, hydrogen, alkyl or cycloalkyl and $R^5$ denotes, for example, hydrogen, alkyl or phenyl, have useful pharmacological properties.

11 Claims, No Drawings

TETRAHYDROQUINOLINE DERIVATIVES, THEIR USE AND PHARMACEUTICAL FORMULATIONS CONTAINING THEM

The invention relates to tetrahydroquinoline derivatives, a process for their preparation, their use as medicines and pharmaceutical formulations containing them.

The present invention relates to derivatives of tetrahydroquinoline of the general formula I

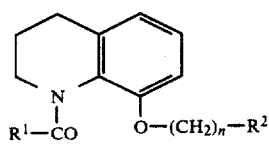

(I)

and acid addition salts thereof, wherein n denotes 2, 3, 4, 5 or 6, $R^1$ denotes alkyl with 1 to 5 C atoms, phenyl, phenyl which is mono-, di- or trisubstituted by alkyl with 1 to 3 C atoms, alkoxy with 1 to 3 C atoms, halogen or trifluoromethyl, thienyl, furyl, pyrrolyl or pyridyl, $R^2$ denotes the radical

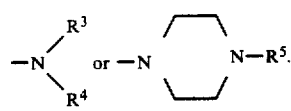

$R^3$ and $R^4$ independently of one another denote hydrogen, alkyl with 1 to 4 C atoms, cycloalkyl with 3 to 8 C atoms or, together with the nitrogen atom to which they are bonded, 1-piperidinyl, 4-morpholinyl, 1-imidazolidinyl or 1-pyrrolidinyl, and $R^5$ denotes hydrogen, alkyl with 1 to 5 C atoms, phenol, phenylalkyl with 1 to 4 C atoms in the alkyl radical, phenoxyalkyl with 1 to 4 C atoms in the alkyl radical, it being possible for the phenyl nuclei present in each case to be mono-, di- or trisubstituted by alkyl with 1 to 3 atoms, alkoxy with 1 to 3 C atoms, halogen or trifluoromethyl, or thienyl, furyl, pyrrolyl, pyridinyl, pyrimidinyl or triazinyl.

Alkyl radicals, including those in association with other radicals, can be straight-chain or branched. Halogen substituents are preferably chlorine or fluorine substituents. Examples of alkyl radicals $R^1$ are: methyl, ethyl, n-propyl, iso-propyl, n-butyl, iso-butyl, sec.-butyl, tert.-butyl, n-pentyl and isopentyl. Substituents for the phenyl $R^1$ are, above all, alkyl and/or alkoxy radicals with in each case 1 to 3 C atoms, and furthermore halogen, in particular fluorine or chlorine, and trifluoromethyl. Examples of suitable substituted phenyl radicals $R^1$ are 2-, 3- or 4-methyl-, -ethyl-, -n-propyl- or -iso-propylphenyl, 2-, 3- or 4-methoxy-, -ethoxy-, -n-propoxy-phenyl, 3,5-dimethyl-phenyl, 3,4,5-trimethyl-phenyl, 3,5-dimethoxy-phenyl, 3,4,5-trimethoxy-phenyl, 2-, 3- or 4-chloro- or -fluoro-phenyl, and 2-, 3- or 4-trifluoromethyl-phenyl. The substituted phenyl radical $R^1$ has, in particular, one alkyl, halogen or trifluoromethyl substituent or one, two or three alkoxy substituents. Thienyl, furyl, pyrrolyl and, preferably, pyridyl are furthermore possible for $R^1$.

The alkyl radicals $R^3$ or $R^4$ are preferably branched. Examples of suitable alkyl radicals are methyl, ethyl, n-propyl, n-butyl, sec.-butyl and, preferably, iso-propyl, iso-butyl and tert.-butyl. Examples of the cycloalkyl radicals $R^3$ or $R^4$ are cyclopropyl, cyclobutyl, cycloheptyl, cyclooctyl and, preferably, cyclopentyl and cyclohexyl.

The phenyl radical in the substituted phenyl, phenylalkyl and phenoxyalkyl radicals $R^5$ can have one, two or three substituents. Examples of suitable substituted phenyl radicals are: 2-, 3- or 4-methyl-, -ethyl-, -n-propyl- or -iso-propyl-phenyl, 2-, 3- or 4-methoxy-, -ethoxy-, -n-propoxyphenyl, 3,5-dimethoxyphenyl, 3,4,5-trimethoxyphenyl, 2-, 3- or 4-chloro- or -fluoro-phenyl and 2-, 3- or 4-trifluoro-methylphenyl. The substituted phenyl radical in the phenyl, phenylalkyl and phenoxyalkyl radicals $R^5$ has, in particular, one alkyl, halogen or trifluoromethyl substituent or one, two or three alkoxy substituents. In the phenylalkyl and phenoxyalkyl radicals $R^5$, the alkyl chain or phenoxyalkyl chain comprises one to four C atoms, in particular two or three C atoms.

Compounds of the general formula I or acid addition salts thereof in which n is 2, 3 or 4, $R^1$ is pyridyl and $R^2$ is a radical $—NR^3R^4$, in which $R^3$ represents hydrogen and $R^4$ denotes the isopropyl, tert.-butyl or cyclohexyl group, are particularly preferred.

The present invention furthermore relates to a process for the preparation of compounds of the formula I, characterized in that (a) a compound of the general formula II

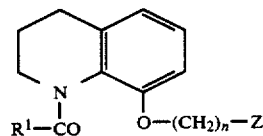

(II)

in which $R^1$ and n have the meanings given and in which Z denotes a group which can be replaced nucleophilically, is reacted with an amine of the general formula III $R^2—H$ (III)

in which $R^2$ has the meaning given, in a manner which is known per se and, if appropriate, the resulting compound is converted with an acid into an acid addition salt, or in that (b) a compound of the general formula IV

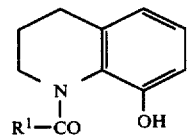

(IV)

in which $R^1$ has the meaning given, is reacted with a compound of the general formula V $R^2—(CH_2)_n—Y$ (V)

in which $R^2$ and n have the meanings given and in which Y denotes a group which can be replaced nucleophilically, in a manner which is known per se and, if appropriate, the resulting compound is converted with an acid into an acid addition salt.

Possible groups Z and Y which can be replaced nucleophilically in the starting substances of the general formulae II and V are, in particular, a chlorine, bromine or iodine substituent or a sulphonic acid radical, preferably a methanesulphonyl, benzenesulphonyl, p-toluenesulphonyl or trifluoromethanesulphonyl radical.

The reaction of the compound of the general formula II with an amine of the general formula III is carried out under the conditions which are known per se for nucleophilic substitution. The reaction here is carried out in a suitable organic solvent in the absence or, preferably, in the presence of an auxiliary base for trapping the acid formed, preferably in the presence of potassium carbonate, sodium carbonate, triethylamine, pyridine, 1,5-diazabicyclo(5,4,0)undec-5-ene or 1,5-diazabicyclo(4,3,0)non-5-ene, and in the presence or absence of an alkali metal halide, preferably sodium iodide or potassium iodide, at a temperature between 0° and 160° C., preferably between 20° and 120° C.

Examples of suitable organic solvents are hydrocarbons, preferably toluene, and preferably, polar organic solvents, thus, for example, lower alcohols, preferably methanol, ethanol, propanol or isopropanol, or lower ketones, preferably acetone, methyl ethyl ketone or methyl isobutyl ketone, or acetonitrile, dimethylformamide, dimethyl sulphoxide or sulpholane.

The reaction of the compound of the general formula IV with the compound of the general formula V is carried out either in a polar aprotic solvent, such as acetonitrile, tetrahydrofuran, dimethyl sulphoxide, dimethylformamide, sulpholane or N-methylpyrrolidone, in the presence of a strong base, such as sodium hydride, potassium hydride, sodium amide, lithium diisopropylamide, butyllithium, potassium tert.-butanolate or lithium hexamethyldisilazide, preferably in dimethylformamide or dimethyl sulphoxide in the presence of sodium hydride, potassium tert.-butanolate or sodium amide, at a temperature between −40° and +100° C., preferably between −20° and +50° C., or in a protic or aprotic polar organic solvent, such as a lower alcohol, for example methanol, ethanol or isopropanol, or a lower ketone, preferably acetone, methyl ethyl ketone or methyl isobutyl ketone, or in dimethylformamide, in the presence of a weak to moderately strong base, such as an alkali metal hydroxide or carbonate or alkaline earth metal hydroxide or carbonate, preferably sodium carbonate or potassium carbonate, or an amine, such as, for example, triethylamine, pyridine, N-ethyldiisopropylamine, 1,5-diazabicyclo(5,4,0)undec-5-ene or 1,5-diazabicyclo(4,3,0)non-5-ene, at a temperature between 0° and 160° C., preferably between 20° and 120° C.

Inorganic and organic acids are suitable for forming acid addition salts with the compounds of the general formula I. Examples of suitable acids are hydrogen chloride, hydrogen bromide, naphthalene-1,5-disulphonic acid and phosphoric, nitric, sulphuric, oxalic, lactic, tartaric, acetic, salicyclic, benzoic, formic, propionic, pivalic, diethylacetic, malonic, succinic, pimelic, fumaric, maleic, malic, sulphamic, phenylpropionic, gluconic, ascorbic, isonicotinic, nicotinic, methanesulphonic, p-toluenesulphonic, citric or adipic acid. Pharmaceutically acceptable acid addition salts are preferred. The acid addition salts can be obtained in the customary manner by combining the components, advantageously in a suitable diluent or dispersing agent.

The starting compounds of the general formula II can be prepared by reaction of compounds of the general formula IV with compounds of the general formula VI $$Y-(CH_2)_n-Z \quad (VI)$$

wherein n, Y and Z have the meanings already given, under the conditions of nucleophilic replacement, such as are described under process variant (b). The reaction product of the formula II thereby formed can be isolated for its further reaction with the compound III, but it can also be further reacted directly without being isolated.

The preparation of the compounds of the general formula IV is known and is described, for example, in European Patent Specification No. 0,025,864.

The compounds of the general formulae III, V and VI are commercially available, known from the literature or accessible by known simple processes from commercially available starting materials.

The compounds of the general formula I according to the invention and pharmaceutically acceptable acid addition salts thereof have useful pharmaceutical properties. In particular, they have antihypertensive and above all antiarrhythmic actions. They are therefore suitable, for example, for treatment of diseases of the cardiovascular system, such as, in particular, for the treatment of cardiac arrhythmia, and furthermore for the treatment of hypertension. Humans can therefore be given the tetrahydroquinolines according to the invention by themselves, as mixtures with one another or in pharmaceutical formulations which contain, as the active constituent, an effective dose of at least one tetrahydroquinoline according to the invention or one pharmaceutically acceptable acid addition salt thereof, in addition to the customary pharmaceutically acceptable excipients and additives.

The compounds of the formula I according to the invention and their pharmaceutically acceptable acid addition salts are effective within a wide dose range. The level of the dose administered depends on the nature of the desired treatment, on the mode of administration and on the state, type and size of the patient treated. In the case of oral dosage, satisfactory results are achieved with doses from 0.01 mg, preferably from 0.1 mg, up to 100 mg, preferably up to 20 mg, of a compound of the formula I per kg of body weight. In humans, the daily dose varies between 1 and 1,200 mg, it being possible to administer individual doses of 0.5 to 400 mg one to three times daily. For intravenous and intramuscular use, the dose is 0.1 to 400 mg daily.

The compounds of the present invention and their pharmaceutically acceptable acid addition salts can be used to produce pharmaceutical preparations which contain an effective amount of the active substance together with pharmaceutically permitted excipients and, if appropriate, additives and are suitable for enteral and parenteral administration. Tablets or gelatine capsules which contain the active compound together with diluents or excipients, for example lactose, dextrose, sucrose, mannitol, sorbitol, cellulose and/or glycine, and lubricants, such as silicic earth, talc, stearic acid or salts thereof, such as magnesium stearate or calcium stearate, and/or polyethylene glycol, are preferably used. If appropriate, tablets contain binders, such as magnesium aluminium silicate, starch, gelatine, tragacanth, methylcellulose, sodium carboxymethylcellulose and/or polyvinylpyrrolidone, and, if necessary, dyestuffs, flavour substances, sweeteners and other auxiliaries or additives. Injectable solutions are preferably isotonic aqueous solutions or suspensions, which can be sterilized and can contain additives or auxiliaries, such as preservatives, stabilizers, wetting and/or emulsifying agents, solubilizers, salts for regulating the osmotic pressure and/or buffer substances. The pharmaceutical preparations according to the invention, which, if desired, can contain other pharmacologically useful substances, are prepared, for example, by means of conventional mixing, granulating the coating processes and contain 0.1 to about 75%, preferably about 1 to about 50%, of the active compound.

The subsequent examples are intended to illustrate the invention, without limiting it to these examples.

EXAMPLE 1

8-(3-(N-Isopropylamino)propoxy)-1-nicotinoyl-1,2,3,4-tetrahydroquinoline oxalate 18.4 g (50.0 mmol) of 8-(3-chloropropoxy)-1-nicotinoyl-1,2,3,4-tetrahydroquinoline hydrochloride are dissolved in 800 ml of dimethylformamide, 8.3 g (50.0 mmol) of potassium iodide and 148 g (2.50 mol) of isopropylamine are added and the mixture is stirred at 80° C. for 3 hours. The reaction solution is then poured onto 3 l of ice-water and extracted several times with methylene chloride. The combined extracts are washed several times with water, dried and concentrated on a rotary evaporator. 13.2 g (74.8%) of oily product remain as the residue.

For conversion into a crystalline derivative, the crude product is dissolved in 40 ml of acetone, a solution of 3.37 g of oxalic acid in 30 ml of acetone is added dropwise and the mixture is subsequently stirred for two hours. The precipitate is filtered off with suction and dried in vacuo. 10.8 g of 8-(3-(N-isopropylamino)propoxy)-1-nicotinoyl-1,2,3,4-tetrahydroquinoline monooxalate of melting point 213°-220° C. are obtained. Analytically pure substance of melting point 215°-219° C. can be obtained by recrystallization from isopropanol.

The 8-(3-chloropropoxy)-1-nicotinoyl-1,2,3,4-tetrahydroquinoline hydrochloride used as the starting substance can be prepared as follows:

7.40 g (0.154 mol) of a 50% strength sodium hydride dispersion are introduced in portions into a solution of 35.6 g (0.14 mol) of 8-hydroxy-1-nicotinoyl-1,2,3,4-tetrahydroquinoline in 200 ml of anhydrous dimethylformamide and the mixture is subsequently stirred at 40°-50° C. for 40 minutes. The reaction solution formed is transferred to a dropping funnel and added dropwise to a solution of 66.0 g (0.52 mol) of 1-bromo-3-chloropropane in 100 ml of anhydrous dimethylformamide at 0° C. The mixture is then stirred at 0° C. for a further hour and subsequently stirred at room temperature for 1 hour and filtered and the solvent and excess 1-bromo-3-chloropropane are distilled off under an oilpump vacuum. The residue is taken up in methylene chloride, the mixture is extracted several times with 1N sodium hydroxide solution and the extract is dried and concentrated.

The oily crude product is further purified by conversion into its hydrochloride as follows: It is taken up in ethyl acetate, a saturated solution of hydrogen chloride in ethyl acetate is slowly added, the mixture is subsequently stirred at room temperature for 2 hours and the precipitate is filtered off with suction, washed with ethyl acetate and dried in vacuo. Yield: 37.9 g (73.7%) of 8-(3-chloropropoxy)-1-nicotinoyl-1,2,3,4-tetrahydroquinoline hydrochloride.

Analytically pure product of melting point 162°-166° C. is obtained by recrystallization from isopropanol.

EXAMPLE 2

8-(3-(4-(2-Methoxyphenyl)piperazin-1-yl)propoxy)-1-nicotinoyl-1,2,3,4-tetrahydroquinoline-trihydrochloride (a) By process variant (a):

3.50 g (9.53 mmol) of 8-(3-chloropropoxy)-1-nicotinoyl-1,2,3,4-tetrahydroquinoline hydrochloride, 2.74 g (11.4 mmol) of 1-(2-methoxyphenyl)piperazine, 2.88 g (28.6 mmol) of triethylamine and 1.58 g (9.53 mmol) of potassium iodide are combined in 50 ml of anhydrous dimethylformamide and the mixture is stirred at 80° C. for 18 hours. After cooling, the reaction solution is poured onto 300 ml of water and extracted twice with methylene chloride. The combined organic phases are then extracted with 2N hydrochloric acid and the acid extracts are rendered basic by addition of concentrated sodum hydroxide solution and extracted again with methylene chloride. These methylene chloride extracts are dried and concentrated and the crude product is further purified by column chormatography on silica gel (mobile phase toluene:ethanol 9:1) 4.2 g (90%) of oily 8-(3-(4-(2-methoxyphenyl)piperazin-1-yl)propoxy)-1-nicotinyl-1,2,3,4-tetrahydroquinoline are obtained.

By dissolving in 30 ml of acetone, adding 30 ml of a saturated solution of hydrogen chloride in diethyl ether and triturating with diethyl ether, 2.4 g of analytically pure 8-(3-(4-(2-methoxyphenyl)piperazin-1-yl)-propoxy)-1-nicotinoyl-1,2,3,4-tetrahydroquinoline-trihydrochloride of melting point 186°-190° C. (decomposition) are obtained therefrom.

(b) By process variant (b):

0.53 (11.0 mmol) of a 50% strength sodium hydride dispersion is introduced in portions into a solution of 2.54 g (10.0 mmol) of 8-hydroxy-1-nicotinoyl-1,2,3,4-tetrahydroquinoline in 20 ml of anhydrous dimethylformamide and the mixture is subsequently stirred at 40°-50° C. for 30 minutes. After cooling to room temperature, a solution of 4.03 g (15.0 mmol) of 1-(3-chloropropyl)-4-(2-methoxyphenyl)piperazine in 20 ml of anhydrous dimethylformamide is added dropwise and the mixture is subsequently stirred at room temperature for 16 hours. The reaction solution is poured onto 150 ml of ice-water and extracted with methylene chloride and the extracts are washed several times with water, dried and concentrated. The crude product is further purified by column chromatography on silica gel (mobile phase toluene:ethanol 9:1) and converted into the dihydrochloride as described under Example 2(a). The product thus obtained is identical to the product described under 2(a).

The following compounds were prepared in accordance with Examples 1 and 2:

EXAMPLE 3

8-(3-(4-(2-(3-Trifluoromethyl-pheoxy)ethyl)-piperazin-1-yl)propoxy)-1-nicotinoyl-1,2,3,4-tetrahydroquinoline oxalate Melting point 216°-220° C. (decomposition).

EXAMPLE 4

8-(2-(N-Isopropylamino)ethoxy)-1-nicotinoyl-1,2,3,4-tetrahydroquinoline oxalate

Melting point 153°-158° C. (decomposition).

EXAMPLE 5

8-(2-(N-tert.-Butylamino)ethoxy)-1-nicotinoyl-1,2,3,4-tetrahydroquinoline oxalate Melting point 154°–160° C. (decomposition).

EXAMPLE 6

8-(2-(N-Cyclohexylamino)ethoxy)-1-nicotinoyl-1,2,3,4-tetrahydroquinoline

Melting point 216°–218° C.

EXAMPLE 7

8-(2-(N-Cyclohexyl-N-methyl-amino)ethoxy)-1-nicotinoyl-1,2,3,4-tetrahydroquinoline oxalate Melting point 130°–131° C. (decomposition).

EXAMPLE 8

8-(4-(N-Isopropylamino)butoxy)-1-nicotinoyl-1,2,3,4,tetrahydroquinoline oxalate

Melting point 160°–163° C.

EXAMPLE 9

8-(4-(4-Methyl-piperazin-1-yl)butoxy)-1-nicotinoyl-1,2,3,4-tetrahydroquinoline dioxalate Melting point 203°–204° C. (decomposition).

EXAMPLE 10

8-(4-Morpholino-butoxy)-1-nicotinoyl-1,2,3,4-tetrahydroquinoline oxalate

Melting point 175°–175° C. (decomposition).

EXAMPLE 11

8-(4-N,N-Dipropylamino-butoxy)-1-nicotinoyl-1,2,3,4-tetrahydroquinoline oxalate

Melting point 128°–134° C.

EXAMPLE 12

8-(3-(4-(2-(3,4-Dimethoxyphenyl)ethyl)-piperazin-1-yl)propoxy)-1-picolinoyl-1,2,3,4-tetrahydrochinoline-trihydrochloride Melting point: 198° C.

EXAMPLE 13

8-(3-(4-(2-(3,4-Dimethoxyphenyl)ethyl)-piperazin-1-yl)propoxy)-1-(3,4,5-trimethoxybenzoyl)-1,2,3,4-tetrahydrochinoline-fumarate Melting point: 166° C.

EXAMPLE 14

8-(3-(4-(2-(3,4-Dimethoxyphenyl)ethyl)-piperazin-1-yl)propoxy)-1-nicotinoyl-1,2,3,4-tetrahydrochinoline Oil.

EXAMPLE 15

8-(3-(N-Cyclohexyl-N-ethyl-amino)propoxy-1-nicotinoyl-1,2,3,4-tetrahydrochinoline-dihydrochloride Melting point: 90° C. (Degradation).

EXAMPLE 16

8-(3-(N,N-Diisopropylamino)propoxy-1-nicotinoyl-1,2,3,4-tetrahydrochinoline-fumarate Melting point: 193° C.

EXAMPLE 17

8-(3-(N-Benzyl-N-methyl-amino)propoxy-1-nicotinoyl-1,2,3,4-tetrahydrochinoline-dihydrochloride Melting point: 75° C. (Degradation).

The antiarrhythmic action of the compounds according to the invention was tested by determination of the contraction force and refractory period on the isolated left atrium of the guinea-pig. For this, guinea-pigs were sacrificed by a blow on the back of the neck, the heart was rapidly removed and the atria were removed and mounted in a thermostatically controlled quadruple organ bath at an initial tension of 1 g. The contraction force of the electrically stimulated atria (frequency 120/minute, voltage about 15 V, pulse width 1 msecond) was detected isometrically with force transducers and the amplified signal was recorded continuously.

A microprocessor-controlled double stimulus generator which triggered off a measurement cycle every 2 minutes 30 seconds was used to measure the refractory period. At the same time, extra stimuli were introduced into the basic rhythm, their delay being automatically increased in 5 msecond steps, starting from 70 mseconds, until an increase in the contraction amplitude of about 25% occurred. The delay time thereby reached was expressed as the refractory period of an on-line data printer.

The substance was administered cumulatively, each dose acting for 15 to 20 minutes. Since the substance effects settle at a plateau towards the end of the action phase, the evaluation was in each case made shortly before administration of the next higher dose. 4 atria were used per substance, each receiving only one substance.

The following table shows that the compounds according to the invention are clearly superior to 8-(3-isopropylamino-2-hydroxy-propoxy)1-nicotinoyl-1,2,3,4-tetrahydroquinoline, the closest prior art (European Pat. No. 0,025,864). The refractory periods are considerably longer with a smaller decrease in the contraction force.

| | $\mu M$ | 10 | 30 | 100 | 300 |
|---|---|---|---|---|---|
| 8-(2-(N—Cyclohexyl-N—methyl-amino)ethoxy)-1-nicotinoyl-1,2,3,4-tetrahydroquinoline oxalate | Δ % refractory period | 35 | 97 | | |
| | Δ % force | −21 | −30 | | |
| 8-(3-(4-(2-Methoxyphenyl)-piperazin-1-yl)propoxy)-1-nicotinoyl-1,2,3,4-tetrahydroquinoline-trihydrochloride | Δ % refractory period | 34 | 76 | | |
| | Δ % force | 0 | −7 | | |
| 8-(4-N,N—Dipropylamino-butoxy)-1-nicotinoyl-1,2,3,4-tetrahydroquinoline oxalate | Δ % refractory period | 35 | 82 | 99 | |
| | Δ % force | 6 | −6 | −28 | |

| | μM | 10 | 30 | 100 | 300 |
|---|---|---|---|---|---|
| 8-(4-Morpholino-butoxy)-1-nicotinoyl-1,2,3,4-tetrahydroquinoline oxalate | Δ % refractory period | 23 | 37 | 60 | 82 |
| | Δ % force | 11 | 13 | 10 | −4 |
| 8-(3-Isopropylamino-2-hydroxypropoxy)-1-nicotinoyl-1,2,3,4-tetrahydroquinoline (Comparison substance - European Patent 0,025,864, Example 1) | Δ % refractory period | | 33 | 61 | |
| | Δ % force | | −18 | −22 | |

EXAMPLE 18

Sugar-coated pills can be prepared in accordance with the following recipe:

| | |
|---|---|
| 8-(3-(4-(2-Methoxyphenyl)piperazin-1-yl)propoxy)-1-nicotinoyl-1,2,3,4-tetrahydroquinoline-trihydrochlorie | 1 mg |
| Corn starch | 100 mg |
| Lactose | 60 mg |
| Secondary calcium phosphate | 30 mg |
| Soluble starch | 3 mg |
| Magnesium stearate | 2 mg |
| Colloidal silicic acid | 4 mg |
| | 200 mg |

EXAMPLE 19

Tablets can be prepared in accordance with the following recipe:

| | |
|---|---|
| 8-(2—N—Cyclohexylamino)-ethoxy)-1-nicotinoyl-1,2,3,4-tetrahydroquinoline | 2 mg |
| Lactose | 60 mg |
| Corn starch | 30 mg |
| Soluble starch | 4 mg |
| Magnesium stearate | 100 mg |

We claim:

1. A tetrahydroquinoline compound of the formula I

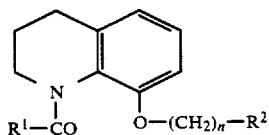

(I)

and acid addition salts thereof, wherein n is selected from the group consisting of 2, 3, 4, 5 and 6, R¹ is selected from the group consisting of alkyl with 1 to 5 C atoms, phenyl, thienyl, furyl, pyrrolyl, pyridyl and phenyl which is mono-, di- or trisubstituted by alkyl with 1 to 3 C atoms, alkoxy with 1 to 3 atoms, halogen or trifluoromethyl, R² is selected from the group consisting of

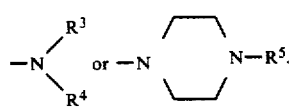

R³ and R⁴ independently of one another are selected from the group hydrogen, alkyl with 1 to 4 C atoms, cycloalkyl with 3 to 8 C atoms or, together with the nitrogen atom to which they are bonded, 1-piperidinyl, 4-morpholinyl, 1-imidazolidinyl and 1-pyrrolidinyl, and R⁵ is selected from the group consisting of hydrogen, alkyl with 1 to 5 C atoms, phenyl, phenylalkyl with 1 to 4 C atoms in the alkyl radical, phenoxyalkyl with 1 to 4 C atoms in the alkyl radical, thienyl, furyl, pyrrolyl, pyridinyl, pyrimidinyl and triazinyl, it being possible for the phenyl nuclei present in each case to be mono-, di- or trisubstituted by alkyl with 1 to 3 C atoms, alkoxy with 1 to 3 C atoms, halogen or trifluoromethyl.

2. Tetrahydroquinoline compounds according to claim 1, characterized in that n is selected from the group consisting of 2, 3 and 4.

3. Tetrahydroquinoline compounds according to claim 1, characterized in that R¹ denotes pyridyl.

4. Tetrahydroquinoline compounds according to claim 1, characterized in that R² denotes the radical —NR³R⁴, wherein R³ represents hydrogen and R⁴ is selected from the group consisting of isopropyl, tert.-butyl and cyclohexyl.

5. Tetrahydroquinoline compounds according to claim 2, characterized in that R² denotes the radical —NR³R⁴, wherein R³ represents hydrogen and R⁴ is selected from the group consisting of isopropyl, tert.-butyl and cyclohexyl.

6. Tetrahydroquinoline compounds according to claim 3, characterized in that R² denotes the radical —NR³R⁴, wherein R³ represents hydrogen and R⁴ is selected from the group consisting of isopropyl, tert.-butyl and cyclohexyl.

7. 8-(2-(N-Cyclohexyl-N-methylamino)ethoxy)-1-nicotinoyl-1,2,3,4-tetrahydroquinoline and pharmaceutically acceptable salts thereof.

8. 8-(3-(4-(2-Methoxyphenyl)-piperazin-1-yl)propoxy)-1-nicotinoyl-1,2,3,4-tetrahydroquinoline and pharmaceutically acceptable salts thereof.

9. 8-(4-N,N-Dipropylamino-butoxy)-1-nicotinoyl-1,2,3,4-tetrahydroquinoline and pharmaceutically acceptable salts thereof.

10. Pharmaceutical formulation for the treatment of cardiac arrhythmia containing an effective dose of a tetrahydroquinoline compound or a pharmaceutically acceptable acid addition salt thereof according to claim 1, in addition to pharmaceutically acceptable excipients and additives.

11. A process for the treatment of cardiac arrhythmia which comprises administering to a host in need thereof an effective amount of a tetrahydroquinoline compound or a pharmaceutically acceptable acid addition salt thereof according to claim 1.

* * * * *